United States Patent [19]
Strebel et al.

[11] Patent Number: 6,147,271
[45] Date of Patent: Nov. 14, 2000

[54] OLIGOMERIZATION PROCESS

[75] Inventors: Allen David Strebel, Westchester, Ill.; Jeffrey Robert Wolf; William Lee Cox, both of Houston, Tex.

[73] Assignee: BP Amoco Corporation, Chicago, Ill.

[21] Appl. No.: 09/201,514

[22] Filed: Nov. 30, 1998

[51] Int. Cl.[7] .................................................. C07C 2/08

[52] U.S. Cl. .................... 585/520; 585/525; 585/903; 526/68

[58] Field of Search ..................................... 585/510, 525, 585/903, 520; 526/68, 67

[56] References Cited

U.S. PATENT DOCUMENTS

| | | | |
|---|---|---|---|
| 4,225,739 | 9/1980 | Nipe et al. | 585/525 |
| 4,239,930 | 12/1980 | Allphin et al. | 585/517 |
| 5,877,375 | 3/1999 | Clarembeau | 585/525 X |
| 6,002,061 | 12/1999 | Clarembeau | 585/525 |

*Primary Examiner*—Fred Teskin
*Attorney, Agent, or Firm*—James R. Henes

[57] ABSTRACT

A process for oligomerizing an acyclic monoolefin monomer in which the oligomerization is controlled to produce predetermined relative amounts of at least two preselected oligomers in a higher boiling fraction of the oligomerization products and the lower boiling products are recycled to the oligomerization reaction.

12 Claims, No Drawings

OLIGOMERIZATION PROCESS

BACKGROUND OF THE INVENTION

1. Field of the Invention

The present invention relates to a process for the oligomerization of an acyclic monoolefin monomer and more particularly concerns the control of the oligomerization reaction to produce predetermined relative amounts of at least two preselected oligomers in a higher boiling fraction of the oligomerization products and the recycle of a lower boiling fraction of the oligomerization products.

2. Discussion of the Prior Art

It is known to recycle certain lower boiling fractions of oligomerization products to the reaction mixture for the oligomerization process in order to increase the yield of higher boiling oligomerization products. For example, European Patent Application No. 349276, filed on Jun. 27, 1989 and published on Jan. 3, 1990, discloses the essentially complete oligomerization of a $C_8$–$C_{12}$ α-olefin and the subsequent removal of the dimer of the $C_8$–$C_{12}$ α-olefin and unreacted $C_8$–$C_{12}$ α-olefin monomer from the oligomerization product, followed by the separation of the trimer from the remaining oligomerization product and combination of a portion of the separated trimer with a $C_8$–$C_{12}$ α-olefin in the reaction mixture in a subsequent oligomerization. The subsequent oligomerization essentially completely converts the $C_8$–$C_{12}$ α-olefin and converts the low viscosity unsaturated trimer to an oligomerization product from which dimer and any unreacted $C_8$–$C_{12}$ α-olefin monomer are removed. The remaining oligomerization product has a medium viscosity.

Nelson et al., U.S. Pat. No. 4,484,014, issued on Nov. 20, 1984, discloses a process in which a branched olefin mixture is oligomerized to produce a lube-oil range hydrocarbon mixture and in which unreacted branched olefins after the oligomerization step or olefins remaining after the lube-oil range hydrocarbon mixture has been separated from the oligomerization mixture may be recycled to the oligomerization step.

Nipe et al., U.S. Pat. No. 4,225,739, issued on Sep. 30, 1980, discloses that light boiling fractions of the oligomerization product are recycled to the oligomerization step in order to increase the yield of the desired heavier oligomerization product, hopefully without degrading the physical properties of the finished product. The patent reports that, in the oligomerization of short chain and long chain 1-olefins in the presence of Friedel-Crafts catalysts to produce super-quality synthetic lubricants, the use of recycle with catalysts such as aluminum chloride did increase the ultimate yield, but the physical properties were either unfavorable or showed little change compared with the properties obtained when recycle was not employed. By contrast, Nipe et al. discloses that when a boron trifluoride catalyst promoted by either water or alcohol was employed, the product yield was essentially unchanged from the yield when recycle was not employed, but the fluid viscosity decreased markedly accompanied by an improvement in viscosity index.

In particular, Nipe et al. discloses a process for producing lubricants having a low viscosity and a high viscosity index that comprises oligomerizing a mixture of short-chain 1-olefins, long chain 1-olefins, and low-boiling recycle from a previous oligomerization run in the presence of boron trifluoride catalyst promoted with water or alcohol. The recycle employed is obtained from a previous oligomerization run and is the overhead fluid fraction obtained when the total oligomerization product is topped to meet a flash point of at least 400° F.

European Patent Application No. 95106749.5, filed May 4, 1995 and published Nov. 8, 1995, discloses a process for the oligomerization of alpha-olefin monomer in which the oligomerization product is fractionated and unreacted alpha-olefin monomer and a portion of the dimers and trimers in the product are separated and recycled to the oligomerization step. The patent application states that the use of recycle in the process results in an improvement in the yield of the higher oligomeric product and permits product properties to be adapted to the respective requirements.

However, none of the aforesaid prior art processes involve both the use of recycle and control of the oligomerization reaction to produce an oligomerization product mixture whose higher boiling fraction contains predetermined relative amounts of at least two preselected oligomers and has a predetermined set of properties such that it can be used directly in or as a synthetic lubricating oil. In fact, only European Patent Application No. 349276A2 discloses the chemical composition of the oligomerization product produced. Furthermore, typically the oligomerization product produced in prior art processes is fractionalized and the composition of the higher boiling fraction is adjusted by the addition or removal of components prior to its being used in or as a synthetic lubricating oil.

Thus, it would be highly desirable to employ recycle of a portion of the oligomerization product mixture and control of the oligomerization reaction in order to improve both the selectivity of the production of an oligomerization product mixture whose higher boiling fraction has a composition and set of properties such that the higher boiling fraction can be used directly in or as a synthetic lubricating oil.

OBJECTS OF THE INVENTION

It is therefore a general object of the present invention to provide an improved aforesaid oligomerization process that affords the aforesaid desirable features and overcomes the aforesaid problems.

More particularly, it is an object of the present invention to provide an aforesaid method that improves the selectivity of the production of predetermined oligomers at preselected relative concentration levels in the higher boiling fraction of the oligomerization product mixture.

It is another object of the present invention to provide an aforesaid method that provides an oligomerization product mixture whose higher boiling fraction has a composition and set of properties such that the higher boiling fraction can be used directly in or as a synthetic lubricating oil.

Other objects and advantages of the present invention will become apparent upon reading the following detailed description and appended claims.

SUMMARY OF THE INVENTION

These objects are achieved by the improvement of the present invention in a process for producing a synthetic hydrocarbon having a predetermined composition comprising: oligomerizing an acyclic monoolefin monomer having from 6 to 30 carbon atoms in the presence of a recycled fraction and an oligomerization catalyst system, under conditions of reaction temperature, pressure, catalyst system composition and concentration and reaction time that are selected such that the ratio of the concentrations of at least two preselected oligomers in the mixture of oligomers produced having molecular weights at least as large as the lowest molecular weight of such preselected oligomers is within a predetermined range of values therefor, and the combination of such at least two oligomers comprises at least about 60 weight percent of those oligomers produced having molecular weights at least as large as the lowest molecular weight of such preselected oligomers; separating the catalyst from the product mixture and terminating the oligomerization either before the ratio of the aforesaid concentrations of the aforesaid at least two preselected oligomers falls outside the predetermined range of values therefor or before the combined concentration of such at least two preselected oligomers comprises less than about 60 weight percent of those oligomers produced having molecular weights at least as large as the lowest molecular weight of such at least two preselected oligomers; separating the oligomerization product mixture into (a) a lower boiling fraction comprising unreacted monomer, oligomers having lower molecular weights than the lowest molecular weight of such preselected oligomers, and optionally a minor portion of oligomers having molecular weights at least as large as the lowest molecular weight of the preselected oligomers and (b) a higher boiling fraction as the synthetic hydrocarbon product and comprising at least a major portion of the oligomers having molecular weights at least as large as the lowest molecular weight of the preselected oligomers; and recycling to the oligomerization step at least a portion of the separated aforesaid lower boiling point fraction as the aforesaid recycled fraction.

DESCRIPTION OF THE PREFERRED EMBODIMENTS

The higher boiling fractions of a number of oligomerization product mixtures can be characterized by their properties and by their compostions. More particularly, the compositions of such higher boiling fractions can be characterized in terms of the presence of certain oligomers in them, the relative concentrations of such certain oligomers in the higher boiling fractions, and the combined concentrations of such certain oligomers in the higher boiling fraction. Therefore, by producing an oligomerization product whose higher boiling fraction has a specific desired aforesaid characterization it is possible to produce a higher boiling fraction which in its entirety has a desired set of properties and can be employed directly in or as a synthetic lubricating oil, without any further adjustments of the composition of the higher boiling fraction by the addition of components to or the removal of components from the higher boiling fraction.

According to the method of the present invention, an oligomerization product whose higher boiling fraction has a certain desired set of properties can be produced highly selectively by conducting the oligomerization reaction under conditions of reaction temperature, pressure, catalyst system composition and concentration and reaction time such that at least two desired oligomers—referred to hereafter as preselected oligomers—are produced and present in the higher boiling fraction, such that the ratio of the concentrations of the at least two preselected oligomers in the mixture of oligomers produced having molecular weights at least as large as the lowest molecular weight of the preselected oligomers is within a predetermined range of values therefor and such that in combined concentrations of the preselected oligomers comprises at least 60 weight percent of the oligomers produced having molecular weights at least as large as the lowest molecular weight of the preselected oligomers.

Acyclic monoolefin monomers that are suitable for use in the method of the present invention include one or more linear alpha olefins, branched alpha olefins, linear internal olefins or branched internal olefins or a mixture thereof. Preferably the acyclic monoolefin monomers are predominantly one or more linear alpha olefins. The acyclic monoolefin monomers employed predominantly contain from six carbon atoms, preferably from eight carbon atoms, to thirty carbon atoms, preferably to fourteen carbon atoms. Minor amounts outside this range can be tolerated as long as they do not adversely affect the physical properties of the oligomers. Thus, suitable linear alpha olefins include 1-hexene, 1-heptene, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-eicosane, 1-docosene, 1-tricosene, and 1-tetracosene.

The oligomerization catalyst system comprises a Friedel-Crafts catalyst and a promoter. Representative Friedel-Crafts catalysts are $BF_3$, $BCl_3$, $AlCl_3$, $AlBr_3$, $SnCl_4$, $GaCl_3$, $FeBr_3$, and the like. Preferably, the catalyst is $BF_3$. Included in the list of substances that are useful as promoters are water, silica gel, aliphatic ethers such as dimethyl ether and diethyl ether, aliphatic alcohols such as methanol, ethanol, propanol, and n-butanol, polyols such as ethylene glycol and glycerol, aliphatic carboxylic esters, ketones, aldehydes and acid anhydrides. Preferably, the promoter is n- butanol, n-propanol or water.

The amount of Friedel-Crafts catalyst employed in the method of this invention should be a catalytic amount, that is an amount which when employed in the presence of a promoter will cause the reaction to proceed at a reasonable rate. A useful of amount of Friedel-Crafts catalyst in the method of this invention is in the range of from about 0.0001 moles, preferably from about 0.005 moles, to about 0.20 moles, preferably to about 0.03 moles of catalyst per mole of monoolefin monomer employed. The amount of promoter employed in the method of this invention is in the range of from about 0.0001 moles, preferably from about 0.0025 moles, to about 0.20 moles, preferably to about 0.025 moles per mole of monoolefin monomer employed.

The oligomerization reaction is conducted at a temperature in the range of from about 0° C., preferably from about 20° C., to about 100° C., preferably to about 60° C., and at a pressure in the range of from about 0 psig, preferably from about 5 psig, to about 725 psig, preferably to about 50 psig.

We have found that the identity and number of the aforesaid preselected oligomers and the aforesaid particular ratio of their individual concentrations vary depending on the monoolefin monomer being oligomerized and the desired properties of the synthetic lubricating oil in which the higher boiling fraction of the oligomerization product is to be employed. For example, in order to oligomerize 1-decene to produce an oligomerization product whose higher boiling fraction is especially suited for use as a synthetic lubricating oil having a viscosity index of 2 cSt, the dimers and trimers are the preselected oligomers, and the oligomerization is conducted such that the ratio of the concentration of trimers to the concentration of dimers in the mixture of oligomers produced is less than about 0.15, preferably less than about 0.1.

As another example, in order to oligomerize 1-decene to produce an oligomerization product whose higher boiling fraction is especially suited for use as a synthetic lubricating oil having a viscosity index of 4 cSt, the trimers and tetramers are the preselected oligomers, and the oligomerization is conducted such that the ratio of the concentration of tetramers to the concentration of trimers in the mixture of oligomers produced is (a) less than about 0.25, preferably less than about 0.23 and (b) greater than about 0.1, preferably greater than about 0.16.

As a further example, in order to oligomerize 1-decene to produce an oligomerization product whose higher boiling fraction is especially suited for use as a synthetic lubricating oil having a viscosity index of 6 cSt, the trimers, tetramers and pentamers are the preselected oligomers, and the oligomerization is conducted such that the ratio of the concentration of pentamers to the concentration of tetramers in the mixture of oligomers produced is (a) less than about 0.55, preferably less than about 0.30, and (b) greater than about 0.15, preferably greater than about 0.2, and the ratio of the concentration of trimers to the concentration of tetramers is (a) less than 0.9, preferably less than or equal to about 0.76, and (b) greater than about 0.55, preferably greater than about 0.6.

Similarly, in order to oligomerize 1-decene to produce an oligomerization product whose higher boiling fraction is especially suited for use as a synthetic lubricating oil having a viscosity index of 8 cSt, the trimers, tetramers and pentamers are the preselected oligomers, and the oligomerization is conducted such that the ratio of the concentration of pentamers to the concentration of tetramers in the mixture of oligomers produced is (a) less than about 0.65, preferably less than about 0.6, and (b) greater than about 0.45, preferably greater than about 0.5, and the ratio of the concentration of trimers to the concentration of tetramers is (a) less than about 0.25, preferably less than or equal to about 0.20, and (b) greater than about 0.08, preferably greater than about 0.12.

Furthermore, in order to oligomerize 1-decene to produce an oligomerization product whose higher boiling fraction is especially suited for use as a synthetic lubricating oil having a viscosity index of 10 cSt, the trimers, tetramers and pentamers are the preselected oligomers, and the oligomerization is conducted such that the ratio of the concentration of pentamers to the concentration of tetramers in the mixture of oligomers produced is (a) less than about 1.0, preferably less than about 0.90, and (b) greater than about 0.65, preferably greater than about 0.75, and the ratio of the concentration of trimers to the concentration of tetramers is (a) less than about 0.10, preferably less than or equal to about 0.05, and (b) greater than about 0.0, preferably greater than about 0.01.

The oligomerization reaction is terminated either before the aforesaid ratio of the aforesaid concentrations of the at least two preselected oligomers falls outside the aforesaid range of values therefor, or before the combination of such at least two preselected oligomers comprises less than about 60 weight percent of the fraction of oligomers produced having molecular weights at least at large as the molecular weights of such at least two oligomers.

When the oligomerization reaction has proceeded to the desired extent, the reaction is terminated and the Freidel-Crafts catalyst system is removed from the oligomerization product. This can be done by any convenient conventional technique, for example, by washing with water or aqueous ammonia.

The lower boiling fraction is then removed from the oligomerization product, for example, by distillation. The lower boiling fraction comprises unreacted monomer, oligomers having lower molecular weights than the lowest molecular weight of the preselected oligomers, and optionally a minor portion (that is, less than about 15 weight percent, preferably less than about 5 weight percent) of the oligomers having molecular weights at least as large as the lowest molecular weight of the preselected oligomers. At least a portion of the separated lower boiling fraction is returned to the oligomerization reactor as the aforesaid recycled fraction. The weight ratio of recycled fraction to fresh monoolefin monomer fed to the oligomerization step is typically in the range of from about 0.1, preferably from about 0.25, to about 5.0, preferably to about 4.0.

The distillation conditions employed are such as to remove as bottom fraction a higher boiling fraction that comprises a major portion (that is, at least about 85 weight percent, preferably at least about 95 weight percent) of the oligomers having molecular weights at least as large as the lowest molecular weight of the preselected oligomers. The higher boiling fraction is the synthetic hydrocarbon product of the method of this invention and has the desired physical characteristics for use as or in a synthetic lubricating oil having specific desired properties. The distillation conditions employed are not intended to effect a change in the composition of the higher boiling fraction.

The present invention will be more clearly understood in connection with the following specific examples, it being understood that the same are for purposes of illustration and not limitation.

EXAMPLE 1

The following example illustrates a low conversion oligomerization of an alpha olefin and recycle of the undesired light cut to maximize production of the desired heavy cut oligomer distribution. For this case the desired product was an oligomer distribution high in $C_{30}$ olefin content. A multipass batch synthesis was used to simulate a continuous recycle process as follows:

(1) A reaction apparatus was set up consisting of a 300 milliliter autoclave with agitator, internal heating/cooling coils, thermocouple and dip leg. A heating and refrigeration bath was used to control the reaction temperature through the internal coils. An external ice/water batch was also used to control the initial heat of reaction. A 100 grams boron triflouride charge cylinder (approximately 500 pounds per square inch gauge) was connected to the vapor space.

(2) To the autoclave, 150.3 grams of 1-decene and 0.34 gram of 1-propanol (0.5 mol %) were added for the first pass reaction.

(3) The bath temperature for the cooling coils was set at 30° C. and the reactor was pressured up to 10 pounds per square inch gauge with boron triflouride.

(4) The reactants were then maintained at 38° C. and 10 pounds per square inch gauge until and while the ratio of the concentrations of $C_{40}$ oligomers to the concentration of $C_{30}$ oligomers was less than 0.25 and the combined concentrations of $C_{30}$ and $C_{40}$ oligomers was at least 60 weight percent of $C_{30+}$ oligomers produced, that is, for a time period of about 15 minutes.

(5) At the end of the 15 minute-period, the reaction was depressurized and purged with nitrogen. The product was then quickly quenched in a 500 milliliter separatory funnel with approximately 150 milliliters of 5 wt % NaOH solution. The organic and aqueous phases were separated and the organic oligomer phase was then washed with approximately 150 milliliters of deionized water in the same separatory funnel. The phases were again separated and the water wash repeated.

(6) The reaction products were analyzed by gas chromatography and found to have the following oligomer distribution:

TABLE 1

| | |
|---|---|
| $C_{10}$ olefin | 55.0 wt% |
| $C_{20}$ olefin | 8.26 wt% |
| $C_{30}$ olefin | 26.8 wt% |
| $C_{40}$ olefin | 6.59 wt% |
| $C_{50+}$ olefin | 3.07 wt% |

The selectivity of the $C_{30}$ olefin relative to the $C_{40+}$ olefin was very high.

The ratio of $C_{30}$ to $C_{40+}$ olefin was 2.77

(7) The reaction product was then flash distilled in a 300 milliliter round bottom flask with a NORMAG condenser at 10–40 millimeters of Hg vacuum to remove the $C_{20}$ and lighter olefin components from the $C_{30+}$ olefin product. A total of 63.5 wt % of the mass was distilled overhead for the first pass with the following gas chromatographic analysis:

TABLE 2

| | Overhead Cut #1 | Overhead Cut #2 | Bottoms Product |
|---|---|---|---|
| $C_{10}$ olefin | 80.6 wt% | 69.5 wt% | 0.00 wt% |
| $C_{20}$ olefin | 11.2 | 18.2 | 18.2 |
| $C_{30}$ olefin | 6.20 | 9.75 | 70.8 |
| $C_{40}$ olefin | 0.97 | 1.44 | 18.8 |
| $C_{50+}$ olefin | 0.24 | 0.39 | 8.07 |

(8) The two overhead cuts from (7) were then combined (90.1 grams) and 9 grams removed to represent a 10% purge for the second pass reaction. The remaining 81.1 grams of overhead product from (7) was combined with 55.0 grams of fresh 1-decene and 0.2 gram 1-propanol (0.35 mole %) and added to the 300 milliliter autoclave. Steps (3) through (7) were then repeated with the above reactants at a 20 pounds per square inch gauge reaction pressure.

(9) The reaction products from the second pass were analyzed by gas chromatography to have the following oligomer distribution:

TABLE 3

| | |
|---|---|
| $C_{10}$ olefin | 42.5 wt% |
| $C_{20}$ olefin | 12.7 wt% |
| $C_{30}$ olefin | 28.5 wt% |
| $C_{40}$ olefin | 12.4 wt% |
| $C_{50+}$ olefin | 3.58 wt% |

Again, the selectivity of the $C_{30}$ olefin relative to the $C_{40+}$ olefin was very high. The ratio of $C_{30}$ to $C_{40+}$ olefin was 1.78. A total of 55 wt % of the mass was distilled overhead on the second pass with the following gas chromatographic analysis:

TABLE 4

| | Overhead Cut | Bottoms Product |
|---|---|---|
| $C_{10}$ olefin | 75.7 wt% | 0.00 wt% |
| $C_{20}$ olefin | 20.6 | 1.88 |
| $C_{30}$ olefin | 3.41 | 61.4 |
| $C_{40}$ olefin | 0.29 | 28.1 |
| $C_{50+}$ olefin | — | 8.51 |

(10) The overhead cut (60 grams) from (9) was then combined with 60 grams of fresh 1-decene and 0.13 gram of 1-propanol (0.25 mol %) and added to the 300 milliliter autoclave for the third pass reaction. Steps (3) through (7) were then repeated with the above reactants at a 20 pounds per square inch gauge reaction pressure.

(11) The reaction products from the third pass were analyzed by gas chromatography to have the following oligomer distribution:

TABLE 5

| | |
|---|---|
| $C_{10}$ olefin | 44.8 wt% |
| $C_{20}$ olefin | 14.9 wt% |
| $C_{30}$ olefin | 28.3 wt% |
| $C_{40}$ olefin | 9.16 wt% |
| $C_{50+}$ olefin | 2.44 wt% |

The ratio of $C_{30}$ to $C_{40+}$ olefin was 2.44. A total of 61 wt % of the mass was distilled overhead on the third pass distillation with the following gas chromatographic analysis:

TABLE 6

| | Overhead Cut | Bottoms Prouct |
|---|---|---|
| $C_{10}$ olefin | 68.4 wt% | 1.72 wt% |
| $C_{20}$ olefin | 22.5 | 1.06 |
| $C_{30}$ olefin | 8.80 | 64.8 |
| $C_{40}$ olefin | 0.26 | 25.7 |
| $C_{50+}$ olefin | — | 6.78 |

(12) The overhead cut (70 grams) from (11) was then combined with 45 grams of fresh 1-decene and 0.12 gram of 1-propanol (0.25 mol %) and added to the 300 milliliter autoclave for the fourth and final pass reaction. Steps (3) through (7) were then repeated with the above reactants. No further analysis was done at this point.

EXAMPLE 2

The following example illustrates a low conversion oligomerization of an alpha olefin and recycle of the undesired light cut to maximize production of the desired heavy cut oligomer distribution. For this case the desired product was an oligomer distribution high in $C_{30}$ oligomer content. A multipass semi-continuous synthesis was used to simulate a continuous recycle process, as follows:

(1) In the first step, a reaction apparatus was set up consisting of one 1 liter autoclave with agitator, internal cooling coil, thermocouple and dip leg. A 10 gallon pressurized feed vessel and positive displacement metering pump were used to continuously feed a mixture of olefin and cocatalyst to the reactor. A pressurized gas cylinder and gas flow controller was also used to feed a continuous stream of boron trifluoride to the reactor. These two streams are premixed before entering the reactor. The reactor outlet flows through a dip leg set at a prescribed height (used to control reaction residence time) into a backpressure regulator used to control the reaction pressure. An automated system was also used to control the temperature of the reactor.

(2) For each reaction pass in the synthesis, a mixture of fresh 1-decene, recycled light cut from the previous pass distillation, and 1-propanol (0.122 wt %) were premixed in the feed vessel. Enough feed was mixed to provide sufficient material for the continuous reaction to reach steady state and still provide sufficient light cut distilled material for the next reaction pass (on the order of 13-18 times the reactor volume).

(3) The reactor was then prepressurized with boron triflouride to 10 pounds per square inch gauge. The backpressure regulator was set to control the reaction pressure at 10 pounds per square inch gauge and a continuous feed of boron triflouride was introduced to the system. The feed rate of boron triflouride was set to exceed 3 grams per hour.

(4) For each step in this synthesis the reactor dip leg was set to provide a reaction volume of 250 milliliters. A continuous feed of olefin/propanol from (2) was then started to the reactor at 1100 milliliters per hour. This feed rate was set to provide a reaction residence time of approximately 13.6 minutes, that is, during the period while the ratio of the concentration of $C_{40}$ oligomers to the concentration of $C_{30}$ oligomers was less than 0.25 and the combined concentrations of $C_{30}$ and $C_{40}$ oligomers was at least 60 weight percent of $C_{30+}$ oligomers produced (approximately 13.6 minutes).

(5) The reaction temperature was controlled at 40° C. throughout the run.

(6) The reaction mass from (5) continuously flowed into a large glass vessel containing 5 wt % NaOH where it was mixed in a nitrogen sparged system. Periodically, the receiving vessel was emptied and the organic oligomers were water washed twice in a large separatory funnel. The washed crude product was then dried in an oven at 60° C. overnight before distillation of the light cut.

(7) After the washed crude product was dried, it was then distilled in a 2" Pope Scientific Wiped Film Still to remove the light cut for recycle back to reaction step (1). Distillation conditions are done at 15 mm Hg vacuum. The goal of the distillation was to remove as much of the $C_{10}$ and $C_{20}$ oligomers without removing the desired $C_{30}$ oligomer. The wiped film still was run at a continuous feed rate of 200 milliliters per hour until all of the crude reaction mass from the previous reaction step was processed.

(8) Once the distillation was complete, the light cut $C_{10}$ and $C_{20}$ oligomers were remixed with fresh 1-decene and 1-propanol for the next reaction by repeating steps (2)–(7). The mixture ratio was controlled at 0.122 wt % 1-propanol plus enough fresh 1-decene to mass balance the bottoms product lost in the previous distillation step. There was also a small purge of light cut olefin from the cycle in order to prevent the buildup of unreactive material.

(9) The desired bottoms olefin product from each pass was then hydrogenated at 425° F. and 400 pounds per square inch gauge in a continuous downflow trickle bed reactor with palladium on alumina catalyst. The products were then analyzed for their physical properties.

(10) Table 7 below summarizes the results of a gas chromatographic analysis from each of the streams in a four pass synthesis along with the mass balance. At the end of the fourth pass, the semi-continuous lab synthesis provides enough information to calculate the percent purge from the recycle stream necessary to stabilize the production rate for a steady state continuous recycle process. The estimated percent purge from the recycle for this series of runs is 15–20 wt %. For each pass, the selectivity of the $C_{30}$ olefin relative to the $C_{40+}$ olefin was very high.

TABLE 7

|  | Pass #1 | Pass #2 | Pass #3 | Pass #4 |
|---|---|---|---|---|
| Crude Reaction Mass |  |  |  |  |
| $C_{10}$ olefin | 73.3 wt% | 72.1 wt% | 71.1 wt% | 69.9 wt% |
| $C_{20}$ olefin | 7.73 | 10.6 | 12.2 | 14.0 |
| $C_{30}$ olefin | 14.7 | 14.0 | 13.7 | 13.4 |
| $C_{40}$ olefin | 3.13 | 2.45 | 2.22 | 2.17 |
| $C_{50+}$ olefin | 1.14 | 0.85 | 0.78 | 0.53 |
| ratio $C_{30}/C_{40+}$ olefin | 3.44 | 4.24 | 4.57 | 4.96 |

TABLE 7-continued

|  | Pass #1 | Pass #2 | Pass #3 | Pass #4 |
|---|---|---|---|---|
| Distilled Overhead |  |  |  |  |
| $C_{10}$ olefin | 89.1 | 84.6 | 86.6 | 83.5 |
| $C_{20}$ olefin | 9.20 | 11.9 | 12.2 | 14.9 |
| $C_{30}$ olefin | 1.61 | 3.38 | 1.05 | 1.43 |
| Distilled Bottoms Product |  |  |  |  |
| $C_{10}$ olefin | 2.55 | 2.46 | 2.58 | 2.57 |
| $C_{20}$ olefin | 2.41 | 5.43 | 6.31 | 10.4 |
| $C_{30}$ olefin | 71.5 | 73.2 | 72.5 | 70.0 |
| $C_{40}$ olefin | 16.3 | 13.6 | 13.2 | 12.4 |
| % Purge from recycle (of total feed) | — | 4.96 wt% | 7.89 wt% | 8.89 wt% |
| % Bottoms Product (of total feed) | 23.4 wt% | 19.8 wt% | 19.2 wt% | 19.8 wt% |
| Distilled Overhead Analysis |  |  |  |  |
| % $C_{10}$ internal olefin | 9.59 wt% | 13.3 wt% | 14.8 wt% | 17.0 wt% |
| % $C_{10}$ paraffin | 0.25 wt% | 0.30 wt% | 0.86 wt% | 0.98 wt% |

(11) Table 8 below summarizes the properties of the distilled and hydrogenated bottoms product from the above four-pass reaction sequence after some of the excess $C_{10}$ and $C_{20}$ oligomers have been removed by distillation from the above distilled bottoms products.

TABLE 8

|  | Pass #2 | Pass #3 | Pass #4 |
|---|---|---|---|
| Product Results |  |  |  |
| 100° C. Viscosity (cst) | 4.15 | 4.11 | 4.04 |
| 40° C. Viscosity (cst) | 18.9 | 18.6 | 18.2 |
| −40° C. Viscosity (cst) | 2850 | 2685 | 2690 |
| Pour Point (° C.) | −70 | −69 | −70 |
| Flash Point (° C.) | 222 | 218 | 220 |
| Bromine No. | <0.1 | 0.07 | 0.05 |
| TAN | <0.01 | <0.01 | <0.01 |
| Specific Gravity | 0.820 | 0.820 | 0.820 |
| NOACK Volatility | 10.3 | N/A | N/A |
| Refractive Index | 1.4565 | 1.4556 | 1.4560 |
| G.C. Analysis |  |  |  |
| $C_{20}$ Paraffin | 0.7 wt% | 0.6 wt% | 0.4 wt% |
| $C_{30}$ Paraffin | 75.2 | 73.4 | 79.4 |
| $C_{40}$ Paraffin | 17.2 | 19.4 | 15.0 |
| $C_{50}$ Paraffin | 6.1 | 6.3 | 4.8 |
| $C_{60}$ Paraffin | 0.8 | 0.3 | 0.5 |
| Average Molecular Weight | 453 | 455 | 447 |

EXAMPLE 3

The following example illustrates a variable study for low conversion oligomerization of an alpha olefin and recycle of the undesired light cut to maximize production of the desired heavy cut oligomer distribution. For this case the desired product was an oligomer distribution high in $C_{30}$ olefin content. The purpose of this experiment was to demonstrate a range of possible conditions and optimize those conditions for the desired $C_{30}$ olefin selectivity.

(1) The experimental apparatus from Example 2 was used to study four different reaction variables on the low conversion oligomerization with recycle process.

(2) For each variable studied, a single pass reaction was performed using a feed made up of fresh 1-decene, recycled light cut ($C_{10}$ and $C_{20}$ olefin) from previous lab runs and 1-propanol. Three levels for each variable were employed during a run with sufficient time between changes to allow the continuous reaction to achieve steady state. By performing the experiment this way, all other variables except one were kept constant during the run.

(3) Tables 9 and 10 below summarize the results from the variable studies. Each variable study represents one run. The results tabulated included the weight average molecular weight of the heavy cut after distillation. For the desired $C_{30+}$ olefin product the optimal weight average molecular weight was approximately 450. The results tabulated include the conversion of $C_{10}$ monomer and the $C_{20}$ olefin content of the crude reaction product before distillation. The optimal results are achieved when the conversion is as high as possible while still minimizing $C_{20}$ olefin production and maintaining a distilled heavy cut weight average molecular weight of 450. No attempt was made in this experiment to optimize the recycle purge, but rather only to keep the feed composition constant for each variable.

TABLE 9

Temperature study
Feed rate = 1050 milliliters per hour
Residence time = 14 minutes
Boron triflouride pressure = 5 pounds per square inch gauge
1-propanol loading = 0.2 wt% of feed

| Temp (° F.) | Conversion (%) | $C_{20}$ Olefin in Crude Reaction Product (wt%) | Weight Average Molecular Weight of Distilled Heavy Cut |
|---|---|---|---|
| 90 | 22.4 | 7.5 | 463 |
| 104 | 26.5 | 8.9 | 454 |
| 118 | 29.8 | 10.7 | 449 |

TABLE 10

Cocatalyst study
Feed rate = 1050 milliliters per hour
Residence time = 14 minutes
Boron triflouride pressure = 10 pounds per square inch gauge
temperature = 118° F.

| 1-propanol (wt%) | Conversion (%) | $C_{20}$ Olefin in Crude Reaction Product(wt%) | Weight Average Molecular Weight of Distilled Heavy Cut |
|---|---|---|---|
| 0.08 | 26.4 | 14.6 | 438 |
| 0.15 | 32.8 | 14.9 | 442 |
| 0.21 | 41.1 | 15.8 | 449 |

TABLE 11

Pressure study
Feed rate = 1100 milliliters per hour
Residence time = 13.6 minutes
1-propanol loading = 0.15 wt % of feed
temperature = 118° F.

| Pressure (psig) | Conversion (%) | $C_{20}$ Olefin in Crude Reaction Product (wt %) | Weight Average Molecular Weight of Distilled Heavy Cut |
|---|---|---|---|
| 5 | 29.5 | 12.1 | 444 |
| 15 | 51.4 | 18.1 | 445 |
| 30 | 51.1 | 13.9 | 452 |

TABLE 12

Residence time study
1-propanol loading = 0.15 wt % of feed
temperature = 118° F.
Boron triflouride pressure = 10 pounds per square inch gauge

| Residence time (min.) | Conversion (%) | $C_{20}$ Olefin in Crude Reaction Product (wt %) | Weight Average Molecular Weight of Distilled Heavy Cut |
|---|---|---|---|
| 8 | 32.4 | 11.1 | 444 |
| 14 | 33.3 | 10.8 | 445 |
| 30 | 34.7 | 11.7 | 454 |

EXAMPLE 4

The following example illustrates a high conversion oligomerization of an alpha olefin to produce a normal oligomer distribution. For this case the desired product was an oligomer distribution high in $C_{30}$ olefin content. The purpose of this example is to demonstrate the advantage of the low conversion with recycle process over the high conversion process to selectively generate the $C_{30}$ oligomer.

(1) In the first step, a reaction apparatus was set up consisting of four one-liter autoclaves in series with agitators, internal cooling coils, thermocouples and dip legs. A 10 gallon pressurized feed vessel and positive displacement metering pump were used to continuously feed a mixture of olefin and cocatalyst to the first reactor in the series. A pressurized gas cylinder and gas flow controller was also used to feed a continuous stream of boron triflouride to the first reactor. These two streams were premixed before entering the reactor. Effluent from a given reactor flows through a dip leg set at a prescribed height (used to control reaction residence time) to the next reactor in the series. Effluent from the fourth reactor flowed into a back-pressure regulator used to control the reaction pressure. An automated system is also used to control the temperature of each of the reactors.

(2) A mixture of fresh 1-decene and 1-propanol (0.11 wt %) was premixed in the feed vessel. Enough feed was mixed to provide sufficient material for the continuous reaction to reach steady state (on the order of 13–18 times the reactor volume).

(3) The reactor was then prepressurized with boron triflouride to 25 pounds per square inch gauge. The backpressure regulator was set to control the reaction pressure at 25 pounds per square inch gauge and a continuous feed of boron triflouride was introduced to the system. The feed rate of boron triflouride was set to exceed 3 grams per hour.

(4) The reactor dip legs were set to provide a reaction volume of approximately 750 milliliters for each reactor. A continuous feed of olefin/propanol from step (2) was then started to the reactor at 1050 milliliters per hour. This feed rate gave a reaction residence time of approximately 170 minutes.

(5) The reaction temperature was controlled at 38° C. throughout the run in each reactor.

(6) Table 13 below summarizes the olefin distribution produced by the reactor system once steady state was achieved. While the distribution peaked at the desired $C_{30}$ olefin, the selectivity of the $C_{30}$ olefin relative to the $C_{40+}$ olefins is much smaller than that of Examples 1 and 2. In order to isolate an 80% pure $C_{30}$ olefin product without $C_{10}$ or $C_{20}$ olefins, two distillations had to be performed. The typical conversion to an 80% pure $C_{30}$ olefin product for the high conversion process was 30–55%. In the low conversion process of Example 2, the conversion to an 80% pure $C_{30}$ olefin product was 80–85%. Also, in Examples 1 and 2, only one distillation step was required. The reaction products were analyzed by gas chromatography to have the following oligomer distribution:

TABLE 13

| | |
|---|---|
| $C_{10}$ olefin | 4.95 wt% |
| $C_{20}$ olefin | 9.05 wt% |
| $C_{30}$ olefin | 48.4 wt% |
| $C_{40}$ olefin | 28.1 wt% |
| $C_{50+}$ olefin | 9.48 wt% |

The ratio of $C_{30}$ to $C_{40+}$ olefins is only 1.29.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

That which is claimed is:

1. A process for producing a synthetic hydrocarbon having a predetermined composition comprising:

oligomerizing an acyclic monoolefin monomer having from 6 to 30 carbon atoms in the presence of a recycled fraction and an oligomerization catalyst system, under conditions of reaction temperature, pressure, catalyst system composition and concentration and reaction time that are selected such that the ratio of the concentrations of at least two preselected oligomers in the mixture of oligomers produced having molecular weights at least as large as the lowest molecular weight of such preselected oligomers is within a predetermined range of values therefor, and the combined concentration of such at least two preselected oligomers comprises at least about 60 weight percent of those oligomers produced having molecular weights at least as large as the lowest molecular weight of such preselected oligomers;

separating the catalyst from the product mixture and terminating the oligomerization either before the ratio of the aforesaid concentrations of the aforesaid at least two preselected oligomers falls outside the predetermined range of values therefor or before the combined concentration of such at least two preselected oligomers comprises less than about 60 weight percent of those oligomers produced having molecular weights at least as large as the lowest molecular weight of such at least two oligomers;

separating the oligomerization product mixture into (a) a lower boiling fraction comprising unreacted monomer, oligomers having lower molecular weights than the lowest molecular weight of such preselected oligomers, and optionally a minor portion of oligomers having molecular weights at least as large as the lowest molecular weight of the preselected oligomers and (b) a higher boiling fraction as the synthetic hydrocarbon product and comprising at least a major portion of the oligomers having molecular weights at least as large as the lowest molecular weight of the preselected oligomers and recycling to the oligomerization step at least a portion of the separated aforesaid lower boiling point fraction as the aforesaid recycled fraction.

2. The process of claim 1 wherein the monoolefin monomer contains from 8 to 14 carbon atoms.

3. The process of claim 2 wherein the monoolefin monomer is an alpha-olefin.

4. The process of claim 3 wherein the monoolefin monomer is a linear alpha-olefin.

5. The process of claim 1 wherein the oligomerization catalyst system comprises a $BF_3$ catalyst and a catalyst promoter.

6. The process of claim 1 wherein from 0.0001 to 0.20 moles of $BF_3$ are employed per mole of monoolefin monomer.

7. The process of claim 5 wherein the promoter is an aliphatic alcohol, aliphatic polyol, aliphatic ether, aliphatic carboxylic ester, ketone, aldehyde or acid anhydride or water.

8. The process of claim 7 wherein the promoter is a primary linear alcohol or water.

9. The process of claim 6 wherein from 0.0001 to 0.20 moles of promoter are employed per mole of monoolefin monomer.

10. The process of claim 1 wherein the oligomerization is performed at a temperature in the range of from about 0° C. to about 100° C.

11. The process of claim 10 wherein the oligomerization is performed at a temperature in the range of from about 20° C. to about 60° C.

12. The process of claim 1 wherein the oligomerization is performed at a pressure in the range of from about 0 to about 725 pounds per square inch gauge.

* * * * *